United States Patent
Ohta et al.

(10) Patent No.: US 7,807,976 B2
(45) Date of Patent: Oct. 5, 2010

(54) RADIATION IMAGE DETECTION APPARATUS AND RADIATION IMAGE PHOTOGRAPHING SYSTEM

(75) Inventors: Yasunori Ohta, Kanagawa (JP); Naoyuki Nishino, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/379,751

(22) Filed: Feb. 27, 2009

(65) Prior Publication Data

US 2009/0220048 A1 Sep. 3, 2009

(30) Foreign Application Priority Data

Feb. 29, 2008 (JP) .............................. 2008-049232

(51) Int. Cl.
*G01T 1/24* (2006.01)
(52) U.S. Cl. ................................. 250/370.09
(58) Field of Classification Search ............. 250/370.09
See application file for complete search history.

(56) References Cited

FOREIGN PATENT DOCUMENTS

| JP | 7140255 | 6/1995 |
|---|---|---|
| JP | 2003210444 | 7/2003 |
| JP | 2006247102 | 9/2006 |
| JP | 2006263339 | 10/2006 |

OTHER PUBLICATIONS

JP 2006-263339 A, machine translation downloaded Sep. 8, 2009 from the Japan Patent Office Advanced Industrial Property Network National Center for Industrial Property Information and Training.*

* cited by examiner

*Primary Examiner*—Constantine Hannaher
(74) *Attorney, Agent, or Firm*—Jean C. Edwards, Esq.; Akerman Senterfitt

(57) ABSTRACT

In a radiation image detection apparatus for reading out a radiation image signal from the radiation detection unit that detects radiation transmitted through a subject and outputting the radiation image signal as a radio communication signal, the carrier frequency of the radio communication signal is made lower during a reading period in which the radiation image signal is being read out by the read out unit than the carrier frequency of the radio communication signal at a time other than the reading period.

5 Claims, 4 Drawing Sheets

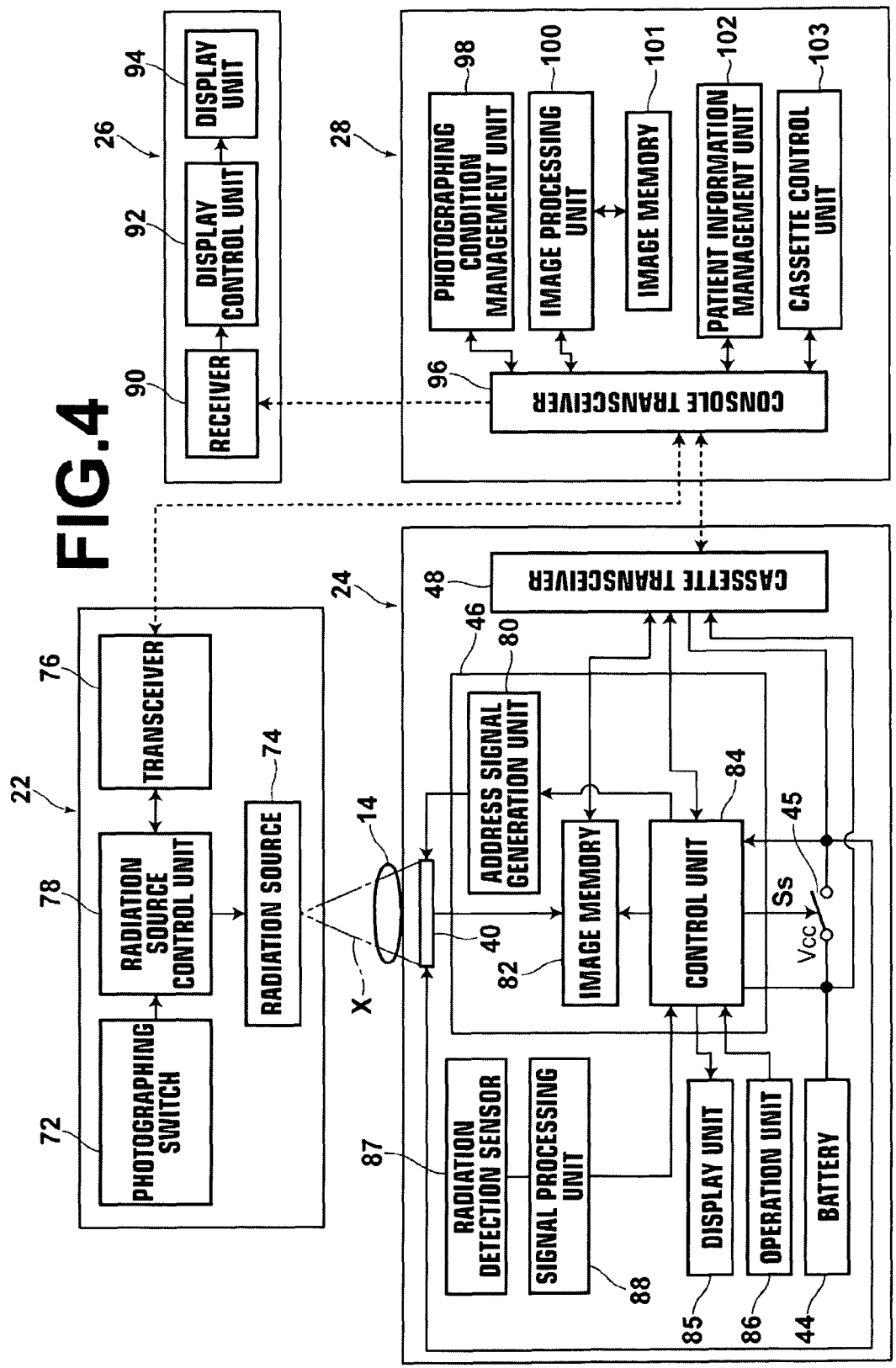

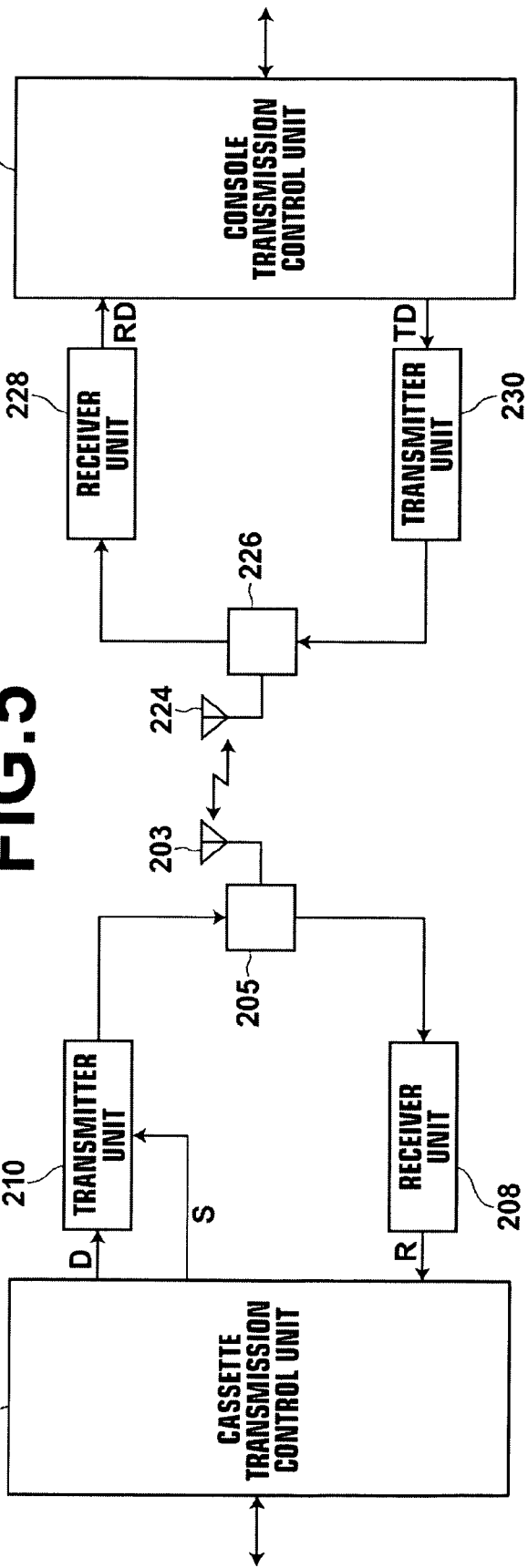

RADIATION IMAGE DETECTION APPARATUS AND RADIATION IMAGE PHOTOGRAPHING SYSTEM

This application claims priority under 35 USC 119 from Japanese Patent Application No. 049232/2008, filed Feb. 29, 2008, the disclosure of which is incorporated by reference herein.

BACKGROUND OF THE INVENTION

1. Field of the Invention

The present invention relates to a radiation image detection apparatus for reading out a radiation image signal from a radiation image detection unit that detects radiation transmitted through a subject and outputting the radiation image signal as a radio communication signal. The invention also relates to a radiation image photographing system having the radiation image detection apparatus.

2. Description of the Related Art

Various types of radiation detectors that record a radiation image of a subject by receiving radiation transmitted through the subject have been proposed and put into practical use in the medical field and the like.

For example, a radiation image detector that uses a semiconductor, such as amorphous selenium or the like, that generates charges by receiving radiation is known, and a so-called optical readout type and a TFT readout type are proposed as such radiation detectors.

As a radiation image photographing system using one of such radiation detectors, Japanese Patent No. 3494683 (Patent Document 1) describes a radiation image photographing system in which radiation image signals detected by the radiation detector are transmitted to a processing unit by radio communication and signal processing, including image processing and the like, is performed in the processing unit.

Further, Japanese Unexamined Patent Publication No. 2006-263339 (Patent Document 2) proposes an electronic cassette that allows high speed radio communication capable of transferring a large volume of radiation image signals rapidly by the use of a high radio frequency.

When outputting radiation image signals as radio communication signals as in Patent Document 1 and Patent Document 2, however, if an already readout radiation image signal is outputted as a radio communication signal while reading out a radiation image signal from the radiation detector, the radiation image signal being read out from the radiation detector is influenced by the radio wave of the radio communication because the radiation image signal being read out is very weak and noise is included in the signal, resulting in degraded image quality of the radiation image.

Consequently, Japanese Unexamined Patent Publication No. 2006-247102 (Patent Document 3) discloses a method in which the operation of a communication module that outputs radio communication signals is stopped while reading out a radiation image signal from the radiation detector.

Further, Japanese Unexamined Patent Publication No. 2003-210444 (Patent Document 4) discloses a method for preventing the influence of radio communication signals on radiation image signals being read out by causing an antenna that emits radio communication signals as a radio wave to have directionality and preventing the radio wave from being emitted to the radiation detector and a detection unit that reads out radiation image signals from the radiation detector.

The method described in Patent Document 3 does not allow radio communication while reading out radiation image signals from the radiation detector, so that the processing speed is reduced. Further, unavailability of radio communication while reading out a radiation image signal from the radiation detector results in that the system is not able to deal with photographing of a preview image or a motion image which requires radiation image signal reading and radio communication to be performed in parallel.

Further, the method described in Patent Document 4 restricts the locations of antennas on the transmit side (electronic cassette) and receive side (console) for the radio communication signals, resulting in unfriendly system.

In view of the circumstances described above, it is an object of the present invention to provide a radiation image detection apparatus and radiation image photographing system capable of preventing the influence of a radio communication signal on a radiation image signal being read out without reducing the processing speed.

SUMMARY OF THE INVENTION

The radiation image detection apparatus of the present invention is an apparatus including a radiation detection unit that generates a charge by receiving radiation transmitted through a subject to detect a radiation image of the subject, a readout unit that reads out a radiation image signal representing the radiation image from the radiation detection unit, and a radio communication unit that outputs a radiation image signal read out from the readout unit as a radio communication signal, wherein the radio communication unit is a unit that causes the carrier frequency of the radio communication signal to become lower during a reading period in which the radiation image signal is being read out by the read out unit than the carrier frequency of the radio communication signal at a time other than during the reading period.

In the radiation image detection apparatus of the present invention described above, the reading period may be a period in which a motion image of the subject is being detected by the radiation detection unit.

Further, the radio communication unit may be a unit that outputs a signal other than the radiation image signal as a radio communication signal, and causes the carrier frequency of the radio communication signal to become lower for the signal other than the radiation image signal than the carrier frequency of the radio communication signal for the radiation image signal during the reading period.

The term "reading period" as used herein refers to a period in which charges generated in the radiation detector by receiving radiation are being taken out as a radiation image signal.

The radiation image photographing system of the present invention is a system including:

a radiation image detection apparatus having a radiation detection unit that generates a charge by receiving radiation transmitted through a subject to detect a radiation image of the subject, a readout unit that reads out a radiation image signal representing the radiation image from the radiation detection unit, and a radio communication unit that outputs a radiation image signal read out from the readout unit as a radio communication signal; and a photographing control apparatus that outputs at least one of a signal indicating still image photographing, a signal indicating preview image photographing, and a signal indicating motion image photographing to the radiation image detection apparatus, wherein:

the radiation image detection apparatus includes a photographing mode signal receiving unit that receives the signal outputted from the photographing control apparatus; and the radio communication unit is a unit that causes the carrier frequency of the radio communication signal to become lower when the signal indicating preview image photographing or the signal indicating motion image photographing is received than the carrier frequency of the radio communication signal when the signal indicating still image photographing is received.

According to the radiation image detection apparatus of the present invention, the carrier frequency of the radio communication signal is made lower during a reading period in which the radiation image signal is being read out by the read out unit than the carrier frequency of the radio communication signal at a time other than during the reading period. This may reduce the influence of a radio communication signal outputted from the radio communication unit on a radiation image signal being read out, so that noise in the radiation image signal may be reduced.

In the radiation image detection apparatus of the present invention, where the carrier frequency of the radio communication signal is made lower for a signal other than the radiation image signal than the carrier frequency of the radio communication signal for the radiation image signal during the reading period, the power consumption of the radio communication may further be saved.

According to the radiation image photographing system of the present invention, the carrier frequency of the radio communication signal is made lower when a signal indicating preview image photographing or a signal indicating motion image photographing is received than the carrier frequency of the radio communication signal when a signal indicating still image photographing is received. This may reduce the influence of a radio communication signal outputted from the radio communication unit on a radiation image signal being read out even in preview image photographing or motion image photographing which requires radiation image signal reading and radio communication to be performed in parallel, so that noise in the radiation image signal may be reduced.

BRIEF DESCRIPTION OF THE DRAWINGS

FIG. 4 is a block diagram of the radiation image photographing system illustrating the configuration thereof.

FIG. 5 is a block diagram of a cassette transceiver in the radiation detection cassette and a console transceiver in a console, illustrating a part of the internal configuration thereof.

DESCRIPTION OF THE PREFERRED EMBODIMENTS

Hereinafter, a radiation image photographing system using an embodiment of the radiation image detection apparatus of the present invention will be described with reference to the accompanying drawings.

Figure 1:
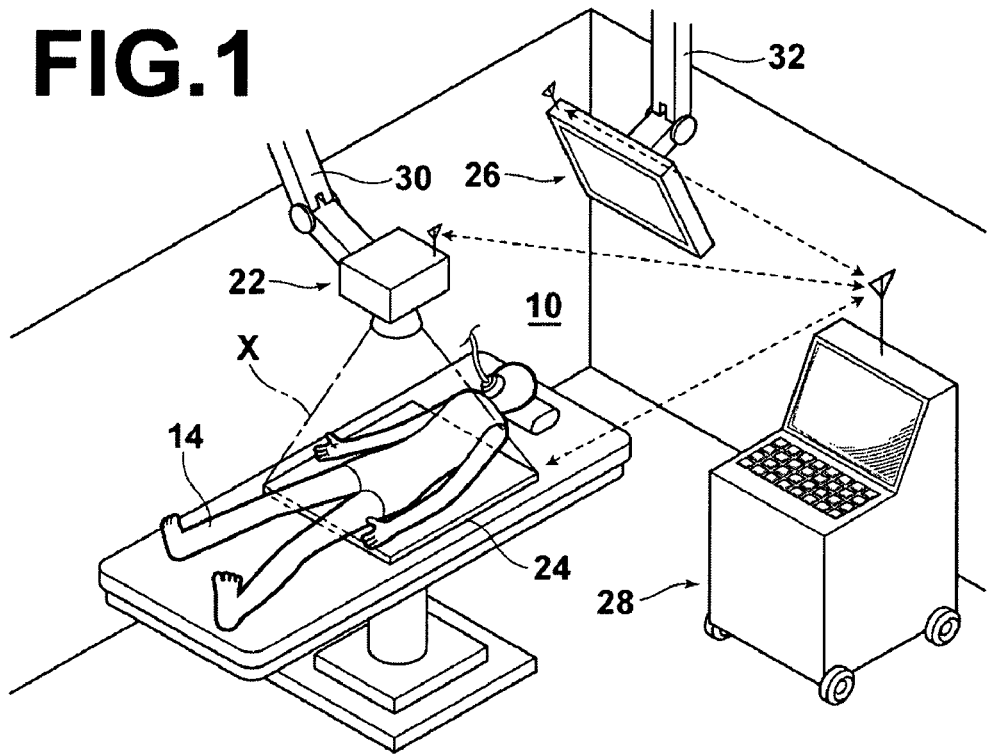
FIG. 1 is a schematic configuration diagram of a radiation image photographing system using an embodiment of the radiation image detection apparatus of the present invention.

FIG. 1 illustrates an appearance of an operating room where radiation image photographing system 10 using an embodiment of the radiation image detection apparatus of the present invention is installed.

Radiation image photographing system 10 includes photographing device 22 that irradiates a dose of radiation X onto patient 14 according to imaging conditions, radiation detection cassette 24 having therein a radiation detector that detects radiation X transmitted through patient 14 and records a radiation image of patient 14, display device 26 that displays the radiation image detected by the radiation detector, and console 28 that controls photographing device 22, radiation detection cassette 24, and display device 26. Console 28 transmits and receives signals to and from photographing device 22, radiation detection cassette 24, and display device 26.

Photographing device 22 is connected to universal arm 30 and is movable to a desired position according to the photographing region of the patient, as well as withdrawable to a position which does not interrupt a surgery by a doctor. Likewise, display device 26 is connected to universal arm 32 and is movable to a position where a photographed radiation image is easily observable by the doctor.

Figure 2:
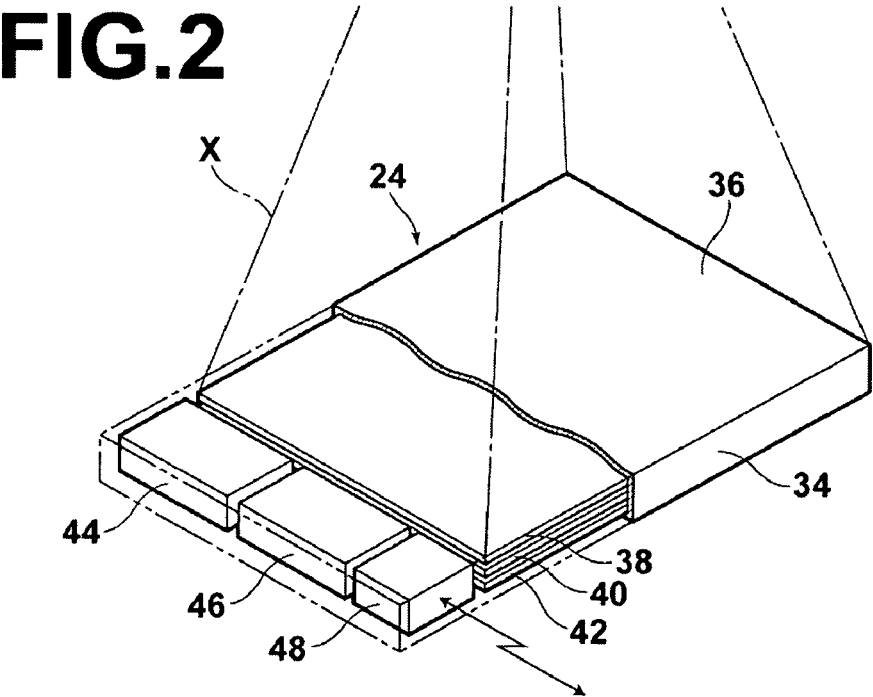
FIG. 2 is an internal configuration diagram of a radiation detection cassette.

FIG. 2 is an internal configuration diagram of radiation detection cassette 24. Radiation detection cassette 24 is provided with casing 34 made of a material that transmits radiation X. Inside of casing 34 are grid 38 that removes scattered rays of radiation X scattered by patient 14, radiation detector 40 that detects radiation X transmitted through patient 14 and records a radiation image of patient 14, and lead plate 42 that absorbs backscattered rays of radiation X disposed from the side of exposure surface 36 of casing 34 where radiation X is irradiated. It is noted that exposure surface 36 of casing 34 may be provided as grid 38.

Casing 34 also includes battery 44 which is the power source of radiation detection cassette 24, cassette control unit 46 that drive controls radiation detector 40 using the power supplied from battery 44, and cassette transceiver 48 that transmits radiation image signals read out from radiation detector 40 and the like to console 28 as radio communication signals and receives control signals and the like from console 28. Preferably, each of cassette control unit 46 and cassette transceiver 48 is provided with a lead plate or the like on the side facing exposure surface 36 of casing 34 in order to prevent damage due to irradiation of radiation X. Although omitted in FIG. 2, radiation detection cassette 24 further includes display unit 85 that displays a radiation image detected by radiation detector 40, operation unit 86 that allows input of a signal for operating radiation detection cassette 24, and the like, as shown in FIG. 4. Still further, radiation detection cassette 24 includes radiation detection sensor 87 that detects irradiated radiation X and signal processing unit 88 that performs predetermined signal processing on the signal detected by radiation detection sensor 87. Based on the signal detected by radiation detection sensor 87, control unit 84 generates a control signal for automatic exposure control, and transmits the control signal to console 28 via cassette transceiver 48.

Figure 3:
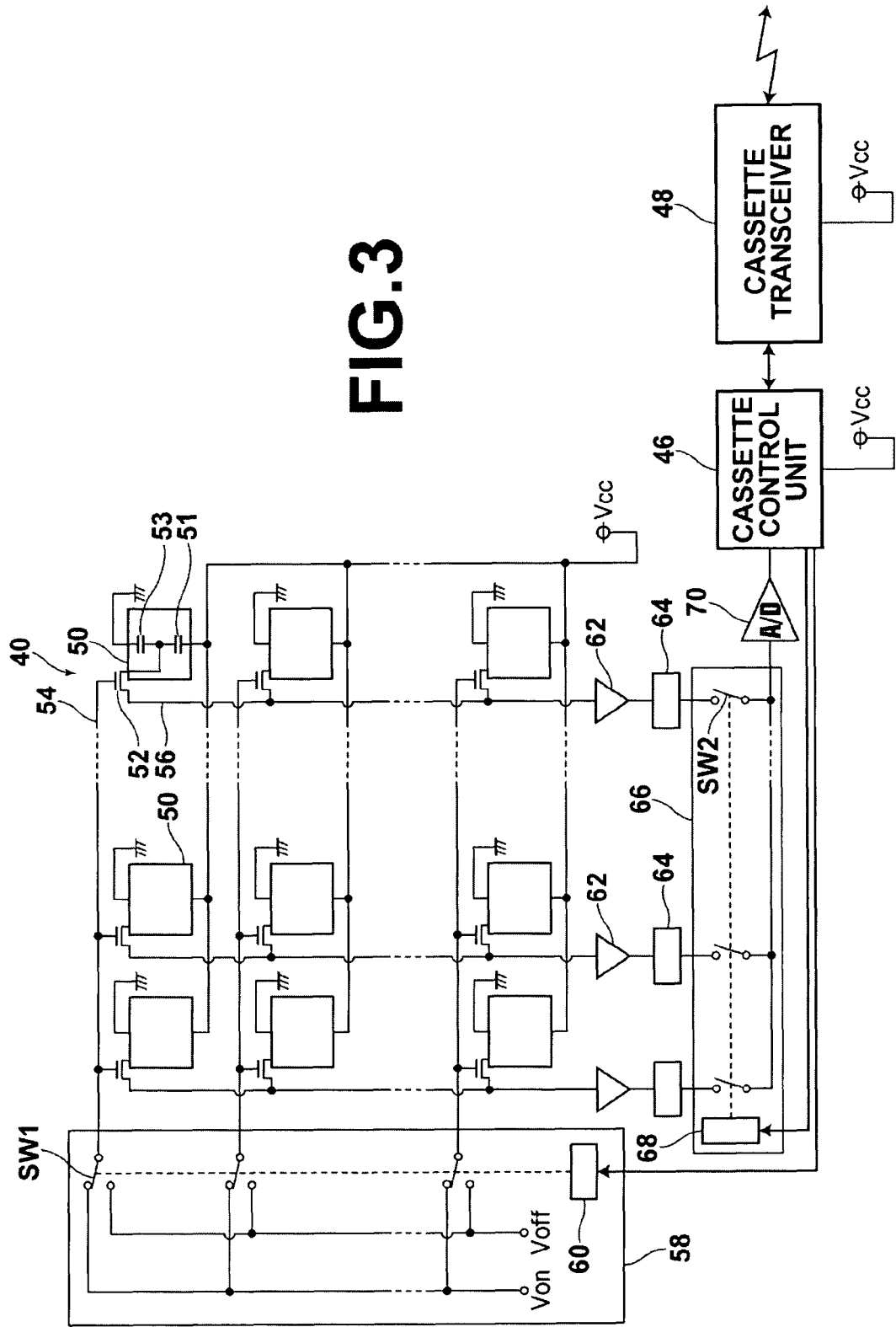
FIG. 3 is a block diagram of a radiation detector illustrating the circuit configuration thereof.

FIG. 3 is a block diagram of radiation detector 40 illustrating the circuit configuration thereof. Radiation detector 40 has a structure in which photoelectrical conversion layer 51 made of a material, such as amorphous selenium or the like, that generates a charge by sensing radiation X is disposed on each of thin film transistors (TFTs) 52 arrayed in a matrix pattern. The charge generated in photoelectrical conversion layer 51 is stored in storage capacitor 53, and TFTs 52 are sequentially turned ON with respect to each row to read out the charges stored in storage capacitors 53 as image signals. It is noted that, in FIG. 3, only the connection aspect between one pixel 50, constituted by photoelectrical conversion layer 51 and storage capacitor 53, and one TFT 52 is shown, and omitted for other pixels 50.

TFT 52 connected to each pixel 50 of radiation detector 40 is provided with gate wire 54 extending in a direction parallel to a row direction and signal wire 56 extending in a direction parallel to a column direction connected thereto. Each gate wire 54 is connected to line scan driving unit 58 and each signal wire 56 is connected to multiplexer 66.

Each gate wire 54 receives control signals Von/Voff for ON/OFF controlling TFTs 52 disposed in a row direction from line scan driving unit 58. Here, line scan driving unit 58 includes a plurality of switches SW1 for switching gate wires 54 and address decoder 60 that outputs a selection signal for selecting one of switches SW1. Address decoder 60 receives an address signal from cassette control unit 46.

Each signal wire 56 receives the charge stored in storage capacitor 53 of each pixel 50 through each of TFTs disposed in a column direction. The charge is amplified by amplifier 62. Each amplifier 62 is connected to multiplexer 66 via sample-and-hold circuit 64. Multiplexer 66 includes a plurality of switches SW2 for switching signal wires 56 and address decoder 68 that outputs a selection signal for selecting one of switches SW2. Address decoder 68 receives an address signal from cassette control unit 46. A/D converter 70 is connected to multiplexer 66 and the radiation image signal converted to a digital signal by A/D converter 70 is outputted to cassette control unit 46.

The internal configurations of photographing device 22, radiation detection cassette 24, display device 26, and console 28 of radiation image photographing system 10 will now be described in detail. FIG. 4 is a block diagram of radiation image photographing system 10 constituted by photographing device 22, radiation detection cassette 24, display device 26, and console 28, illustrating the configuration thereof.

Photographing device 22 includes photographing switch 72, radiation source 74 that emits radiation X, transceiver 76 that receives photographing conditions from console 28 by radio communication and transmits a photographing complete signal to console 28 by radio communication, and radiation source control unit 78 that controls radiation source 74 based on a photographing start signal supplied from switch 72 and the photographing conditions supplied from transceiver 76. Where the automatic exposure control is performed based on the signal detected by radiation detection sensor 87 as described above, a control signal generated based on the signal detected by radiation detection sensor 87 is outputted from cassette control unit 46 to console 28 via cassette transceiver 48, and a control signal is outputted from console 28 to photographing device 22 and inputted to radiation source control unit 78 via transceiver 76. Then, radiation source control unit 78 causes radiation source 74 to stop emitting radiation based on the control signal.

Radiation image photographing system 10 is configured to allow photographing in one of three photographing modes of preview image photographing, motion image photographing, and still image photographing. Photographing mode selection can be implemented at console 28, and a control signal according to the selected photographing mode is outputted from console 28 to photographing device 22 and radiation detection cassette 24. Then, the control signal is inputted to radiation source control unit 78 of photographing device 22 via transceiver 76, and radiation source control unit 78 controls the emission of radiation from radiation source 74 based on the control signal.

Radiation detection cassette 24 includes, as described above, radiation detector 40, battery 44, cassette control unit 46, cassette transceiver 48, and power switch 45. Power switch 45 is ON/OFF switched by control signal Ss from control unit 84 and the power from battery 44 is supplied to radiation detection unit 46, cassette control unit 46, and cassette transceiver 48. Control unit 84 outputs control signal Ss to power switch 45 based on a control signal outputted from console 28 and inputted thereto via cassette transceiver 48.

Cassette control unit 46 includes address signal generation unit 80 that supplies address signals to address decoder 60 of line scan driving unit 58 and address decoder 68 of multiplexer 66 in radiation detector 40, image memory 82 that stores a radiation image signal read out from radiation detector 40, and control unit 84 that controls the operation of address signal generation unit 80, image memory 82, and cassette transceiver 48.

Control unit 84 outputs a signal indicating that a radiation image signal is being read out from radiation detector 40 to cassette transceiver 48, as described later. In addition, control unit 84 outputs various types of information within radiation detection cassette 24, including an operational status of radiation detector 40 other than under reading operation, to console 28 via cassette transceiver 48. Further, control unit 84 receives various control signals, as well as the control signal for switching ON power switch 45, from console 28 via cassette transceiver 48. Radiation image photographing system 10 according to the present embodiment allows setting of the photographing mode of preview image photographing, motion image photographing or still image photographing at console 28. The information indicating the selected photographing mode is also outputted from console 28 and inputted to control unit 84 via cassette transceiver 48, and control unit 84 controls address signal generation unit 80, image memory 82, and the like based on the information.

Display device 26 includes receiver 90 that receives radiation image signals from console 28, display control unit 92 that performs display control of the received radiation image signals, and display unit 94 that displays a radiation image based on radiation image signals processed by display control unit 92.

Console 28 includes console transceiver 96 that transmits and receives necessary information, including radiation image signals, by radio communication to and from photographing device 22, radiation detection cassette 24, and display device 26; imaging condition management unit 98 that manages required photographing conditions for the photographing by photographing device 22; image processing unit 100 that performs image processing on radiation image signals transmitted from radiation detection cassette 24; image memory 101 that stores the image processed radiation image signals; patient information management unit 102 that manages patient information of a photographing target, patient 14; and cassette control unit 103 that outputs various control signals, including the control signal for switching ON power switch 45 and signal representing photographing mode information, to radiation detection cassette 24, and receives various types of information within radiation detection cassette 24, including the operational status of radiation detector 40, from radiation detection cassette 24.

The photographing conditions are conditions to determine the tube voltage, tube current, exposure time, and the like for exposing the photographing region of patient 14 with an appropriate dose of radiation X. For example, the photographing region, photographing method, and the like may be cited as the conditions. The patient information is information for identifying patient 14, such as the name, gender, patient ID number. Photographing order information, including these imaging conditions and the patient information may be set at console 28.

Further, as described above, a photographing mode can be selected for the photographing from the three photographing modes of preview image photographing, motion image photographing, and still image photographing at console 28, and console 28 outputs a control signal according to the selected photographing mode to photographing device 22 and radiation detection cassette 24.

FIG. 5 is a block diagram of cassette transceiver 48 in radiation detection cassette 24 and console transceiver 96 in console 28, illustrating a part of the internal configuration thereof.

Cassette transceiver 48 in radiation detection cassette 24 includes cassette transmission control unit 202 having a microcomputer, antenna 203, antenna duplexer 205, receiver unit 208, and transmitter unit 210.

Receiver unit 208 receives and demodulates a radio wave captured by antenna 203 via antenna duplexer 205 and outputs the demodulated signal to cassette transmission control unit 202 as received signal R. Transmitter unit 210 modulates and outputs radiation image signals D read out from image memory 82 (FIG. 4) and outputted from cassette transmission control unit 202 at a predetermined transfer rate. Transmitter unit 210 is configured modulate the signals based on two different carrier frequencies, and the two carrier frequencies are switched from one to the other according to control signal S from cassette transmission control unit 202. Cassette transmission control unit 202 sets the carrier frequency of the radiation image signal lower during a reading period in which the radiation image signal is being read out from radiation detector 40 than the carrier frequency of the radiation image signal at a time other than during the reading period according to a signal from control unit 84 (FIG. 4). Hereinafter, the carrier frequency during the reading period in which the radiation image signal is being read out is referred to as "reading period carrier frequency" and the carrier frequency at a time other than during the reading period is referred to as "normal time carrier frequency".

As for the reading period carrier frequency and normal time carrier frequency, for example, a frequency in the 400 MHz band authorized as the medical band may be used as the reading period carrier frequency, and a frequency in the 2.4 GHz band or 5.8 GHz band authorized as the ISM band may be used as the normal time carrier frequency.

Preferably, the reading period carrier frequency is set to a value that the radio communication signal outputted from cassette transceiver 48 does not influence the radiation image signal being read out. The term "a value that the radio communication signal does not influence the radiation image signal being read out" refers to a value that the radiation image signal being read out does not pick up noise influenced by the radio communication signal or may pick up noise but is not appreciable.

The reading period carrier frequency may be determined, for example, in the following manner. That is, while outputting the radio communication signal from radiation detection cassette 24, detecting the amount of noise in the radiation image signal being read out and determining the carrier frequency when the amount of noise is reduced to less than a predetermined threshold value as the reading period carrier frequency.

In the mean time, console transceiver 96 includes console transmission control unit 220 having a microcomputer, antenna 224, antenna duplexer 226, receiver unit 228, and transmitter unit 230. Receiver unit 228 receives and demodulates a radio wave captured by antenna 224 via antenna duplexer 226 and outputs the demodulated signal to console transmission control unit 220 as received signal RD. Transmitter unit 230 modulates and outputs signal TD outputted from console transmission control unit 220.

Next, an operation of radiation image photographing system 10 using an embodiment of the radiation image detection apparatus of the present invention will be described.

Radiation image photographing system 10 is installed in operating room 12 and used, for example, when photographing of a radiation image is required by a doctor during a surgery of a patient. For that purpose, patient information of a photographing target, patient 14, is registered in patient information management unit 102 in console 28 in advance prior to the photographing. Where the photographing region and photographing method are predetermined, these photographing conditions are registered in imaging condition management unit 98 in advance. After these preparations are completed, the surgery is performed on patient 14.

When photographing a radiation image during the surgery, the doctor or a radiographer places radiation detection cassette 24 in a predetermined position between patient 14 and operating table 16 with exposure surface 36 on the side of photographing device 22.

Then, the doctor or radiographer operates console 28 to output control signal for switching ON power switch 45 of radiation detection cassette 24 from cassette control unit 103 in console 28, which is outputted from console 28 via console transceiver 96. Then, the control signal is received by cassette transceiver 48 in radiation detection cassette 24 and outputted to control unit 84, whereby a control signal is outputted from control unit 84 to power switch 45 and power switch 45 is switched ON. When power switch 45 in radiation detection cassette 24 is switched ON, signals representing various types of information within the radiation detection cassette 24, including the operational status of radiation detector 40, are outputted from control unit 84 of cassette control unit 46, which are outputted to console 28 via cassette transceiver 48.

Here, signals representing various types of information within the radiation detection cassette 24 are outputted from cassette transmission control unit 202 to transmitter unit 210 in cassette transceiver 48 at a predetermined transfer rate. Then, the signals are modulated in transmitter unit 210 and outputted toward console 28 via antenna duplexer 205 and antenna 203. At this time, the carrier frequency in transmitter unit 210 is set to the normal time carrier frequency, since cassette transmission control unit 202 does not receive the signal indicating that a radiation image signal is being read out from radiation detector 40.

Next, photographing device 22 is moved to a position opposite to radiation detection cassette 24 and photographing is performed by operating photographing switch 72.

Radiation source control unit 78 in photographing device 22 obtains imaging conditions related to the photographing region of patient 14 from imaging condition management unit 98 in console 28 by radio communication via console transceiver 96 and transceiver 76. Then radiation source control unit 78 controls radiation source 74 according to the obtained imaging conditions, whereby radiation X of predetermined dose is irradiated on patient 14. Here, an operation when the still image photographing mode is selected at the console will be described.

Radiation X transmitted through patient 14 is irradiated on radiation detector 40 after scattered rays thereof are removed by grid 38 of radiation detection cassette 24, which is converted to an electrical signal by photoelectrical conversion layer 51 of each pixel 50 constituting radiation detector 40 and stored in storage capacitor 53 as a charge (FIG. 3).

Here, radiation X irradiated toward radiation detection cassette 24 is also detected by radiation detection sensor 87 in radiation detection cassette 24. Where automatic exposure control is performed based on the signal detected by radiation detection sensor 87, an automatic exposure control signal generated based on the signal detected by radiation detection sensor 87 is outputted from control unit 84 in cassette control unit 46 to console 28 via cassette transceiver 48. Here also, cassette transmission control unit 202 in cassette transceiver 48 does not receive the signal indicating that a radiation image signal is being read out from radiation detector 40, so that the carrier frequency of transmitter unit 210 is set to the normal time carrier frequency.

In response to the automatic exposure control signal transmitted from radiation detection cassette 24, a control signal is outputted from console 28 to photographing device 22 and inputted to radiation source control unit 78 via transceiver 76. Then, radiation source control unit 78 causes radiation source 74 to stop emitting radiation based on the control signal.

After the irradiation of radiation X is completed in the manner as described above, the charge signal stored in each storage capacitor 53 of radiation detector 40 is read out according to address signals supplied from address signal generation unit 80 constituting cassette control unit 46 to line scan driving unit 58 and multiplexer 66.

That is, address decoder 60 in line scan driving unit 58 outputs a selection signal to select one of switches SW1 according to the signal supplied from address signal generation unit 80, thereby supplying control signal Von to the gates of TFTs 52 connected to the corresponding gate wire 54. In the mean time, address decoder 68 in multiplexer 66 outputs selection signals to sequentially select switches SW2 according to the signal supplied from the address signal generation unit 80, thereby sequentially reading out the signal charge stored in storage capacitor 53 of each pixel 50 connected to the gate wire 54 selected by line scan driving unit 58 via each signal wire 56.

The signal charge read out from storage capacitor 53 of each pixel 50 connected to the selected gate wire 54 of radiation detector 40 is amplified by each amplifier 62 connected to each signal wire 56, sampled by each sample-and-hold circuit 64, and supplied to A/D converter 70 where the signal charges are converted to a digital signal. The radiation image signal converted to digital signal is tentatively stored in image memory 82 in cassette control unit 46.

Address decoder 60 in line scan driving unit 58 sequentially select switches SW1 according to the signal supplied from address signal generation unit 80, whereby the charge signal stored in storage capacitor 53 of each pixel 50 connected to each gate wire is read out via each signal wire 56 and stored in image memory 82 in cassette control unit 46 via multiplexer 66 and A/D converter 70 in the same manner as described above.

Then, control unit 84 in cassette control unit 46 reads out image signals for one frame by controlling radiation detector 40 in the manner as described above and tentatively stores the image signals in image memory 82.

After the reading and storage of the radiation image signals are completed for one frame, control unit 84 in cassette control unit 46 sequentially reads out the radiation image signals from image memory 82 and outputs to cassette transceiver 48.

Cassette transmission control unit 202 in cassette transceiver 48 outputs the inputted transmission unit of radiation image signals to transmitter unit 210 at a predetermined transfer rate. Then, the radiation image signals are modulated in transmitter unit 210 and transmitted to console 28 via antenna duplexer 205 and antenna 203 as radio communication signals.

In the still image photographing mode, radiation image signals for one frame are read out first, and then the radiation image signals are outputted as radio communication signals as described above, so that the radio communication signals do not influence a radiation image signal being read out. In addition, when outputting the radiation image signals as the radio communication signals, the signal indicating that a radiation image signal is being read out is not outputted from control unit 84, so that the carrier frequency in transmitter unit 210 is set to the normal time carrier frequency by cassette transmission control unit 202.

The modulated signals transmitted to console 28 are demodulated as radiation image-signals by console transceiver 96 in console 28, and the radiation image signals are subjected to predetermined image processing by image processing unit 100 and stored in image memory 101 associated with patient information of patient 14 registered in patient information management unit 102.

Thereafter, the image-processed radiation image signals are transmitted from console transceiver 96 to display device 26. In display device 26, receiver 90 receives the radiation image signals and display unit 94 displays a radiation image under control of display control unit 92.

In the description above, after the reading and storage of the radiation image signals for one frame are completed, the radiation image signals are sequentially read out from image memory 82 and outputted to cassette transceiver 48 by control unit 84 in cassette control unit 46. For example, where a unit of radiation image signals for transmission is stored in image memory 82 before radiation image signals for one frame are stored therein, the unit of radiation image signals may be sequentially read out from image memory 82 and outputted to cassette transceiver 48. In this case, however, the signal indicating that a radiation image signal is being read out is outputted from control unit 84, the carrier frequency in transmitter unit 210 is set to the reading period carrier frequency by cassette transmission control unit 202. Then, after the reading of the radiation image signal is completed, the carrier frequency in transmitter unit 210 is reset to the normal time carrier frequency by cassette transmission control unit 202. Accordingly, a radiation image signal still remaining in image memory 82 after the reading of the radiation image signal is completed is transmitted by the normal time carrier frequency.

Next, an operation when the preview image photographing mode is selected at console 28 will be described.

The operation process until the start of irradiating radiation X onto patient 14 is identical to that in the still image photographing mode described above.

In the preview image photographing mode, automatic exposure control, as in the still image photographing mode, is not performed and radiation X is continuously irradiated on patient 14 until an instruction to terminate the photographing is issued from console 28.

Radiation X transmitted through patient 14 is irradiated on radiation detector 40 in radiation detection cassette 24 and charges are stored in storage capacitors 53 of radiation detector 40 in the same manner as described above.

Then, the charge signal stored in each storage capacitor 53 is readout according to address signals supplied from address signal generation unit 80 constituting cassette control unit 46 to line scan driving unit 58 and multiplexer 66. The reading operation is identical that described above.

The radiation image signal converted to digital signal is tentatively stored in image memory 82 in cassette control unit 46.

When a unit of radiation image signals for transmission is stored in image memory 82 before radiation image signals for one frame are stored therein, control unit 84 of cassette control unit 46 sequentially reads out the unit of radiation image signals and outputs to cassette transceiver 48. It is noted that, in the preview image photographing mode, a radiation image signal tentatively stored in image memory 82 is erased when read out and does not remain in image memory 82.

Cassette transmission control unit 202 in cassette, transceiver 48 outputs the inputted transmission unit of radiation image signals to transmitter unit 210 at a predetermined transfer rate. Then, the radiation image signals are modulated in transmitter unit 210 and transmitted to console 28 via antenna duplexer 205 and antenna 203 as radio communication signals.

Here, in the preview image photographing mode, reading of a radiation image signal from radiation detector 40 and transmission of radio communication signals to console 28 are performed in parallel, the radio communication signals may possibly influence the radiation image signal being read out.

Therefore, control unit 84 in cassette control unit 46 outputs a signal indicating that a radiation image signal is being read out while a radiation image signal is being read out from radiation detector 40. The signal is inputted to cassette transmission control unit 202 in cassette transceiver 48, and cassette transmission control unit 202 outputs a control signal to transmitter unit 210 according to the signal and the transmitter unit 210 reduces the carrier frequency to the predetermined reading period carrier frequency.

The modulated signals transmitted to console 28 are demodulated as radiation image signals by console transceiver 96 in console 28, and the radiation image signals are subjected to predetermined image processing by image processing unit 100 and stored in image memory 101 associated with patient information of patient 14 registered in patient information management unit 102.

Thereafter, the image-processed radiation image signals are transmitted from console transceiver 96 to display device 26. In display device 26, receiver 90 receives the radiation image signals and display unit 94 displays a radiation image under control of display control unit 92.

In the preview image photographing mode, the irradiation of radiation and reading of radiation image signals are performed continuously until an instruction to terminate the photographing is issued from console 28 as described above, so that the operation process described above is repeated and preview images are displayed on display unit 94 in display device until the instruction to terminate the photographing is issued from console 28.

Thereafter, when the instruction to terminate the preview image photographing is issued from console 28, a control signal for terminating the operation of radiation detection cassette 24 is outputted from cassette control unit 103 in console 28 and outputted from console 28 via console transceiver 96. The control signal is received by cassette transceiver 48 in radiation detection cassette 24 and outputted to control unit 84. Then, a control signal is outputted from control unit 84 to address signal generation unit 80 and address signal generation unit 80 terminates the reading of radiation image signals from radiation detector 40. In the mean time, when the instruction to terminate the preview image photographing is issued, a control signal is outputted from console 28 also to photographing device 22 as a radio communication signal. Photographing device 22 receives the control signal via transceiver 76 and radiation source control unit 78 causes the radiation source 74 to stop emitting radiation X in response to the control signal.

After reading of radiation image signals from radiation detector 40 is completed, that is, when the signal indicating that radiation detector 40 is under reading operation is not outputted from control unit 84 in cassette control unit 46, cassette transmission control unit 202 outputs a control signal to transmitter unit 210 to increase the carrier frequency in transmitter unit 210 to the normal time carrier frequency.

Next, an operation when the motion image photographing mode is selected at console 28 will be described.

The operation in the motion image photographing mode is nearly identical to that in the preview image photographing mode. It differs from the operation in the preview image photographing mode in that a radiation image signal tentatively stored in image memory 82 remains therein without being erased.

The radiation image signals stored in image memory in the motion image photographing mode are read out at any desired time and outputted as radio communication signals via cassette transceiver 48. But reading of a radiation image signal from radiation detector 40 is not performed at this time, so that the carrier frequency in transmitter unit 210 is set to the normal time carrier frequency by cassette transmission control unit 202 in cassette transceiver 48.

In radiation image photographing system 10 according to the present embodiment, while a radiation image signal is being read out from radiation detector 40, a signal indicating that radiation detector 40 is under reading operation is outputted from control unit 84 in cassette control unit 46, and the carrier frequency in transmitter unit 210 is reduced to the reading period carrier frequency by cassette transmission control unit 202 in response to the signal, but the signal indicating that radiation detector 40 is under reading operation is not necessarily outputted from control unit 84.

For example, an arrangement may be adopted in which a signal indicating one of the photographing modes is outputted from console 28 to radiation detection cassette 24, and the carrier frequency is switched between the reading period carrier frequency and normal time carrier frequency according to the signal. More specifically, when a signal indicating the still image photographing mode is received by control unit 84 in radiation detection cassette 24, the carrier frequency in transmitter unit 210 is maintained in the normal time carrier frequency, while a signal indicating the preview image photographing mode or motion image photographing mode is received, control unit 84 in radiation detection cassette 24 receives a signal instructing to terminate the photographing to switch the carrier frequency in transmitter unit 210 to the reading period carrier frequency until transmission of radiation image signals representing photographed preview images or motion image is completed. In the still image photographing mode, it is assumed that transmission is started after radiation image signals for one frame are tentatively stored in image memory 82, that is, after reading of the radiation image signals are completed.

Further, in the radiation image photographing system of the present embodiment, when photographing of radiation image is not performed at all, that is, when transmitting a signal other than a radiation image signal as a radio communication signal from radiation detection cassette 24, the carrier frequency in transmitter unit 210 may be set lower than the reading period carrier frequency. A lower carrier frequency allows saving of the power consumption.

Still further, in the radiation image photographing system of the present embodiment, the carrier frequency of radiation detection cassette 24 is changed by taking into account the influence of radio communication signals transmitted therefrom on a radiation image signal being read from radiation detector 40. Further, the carrier frequency of console 28 may be determined by taking into account the influence of control signals transmitted therefrom on a radiation image signal being read from radiation detector 40. The control signals transmitted from console 28 to radiation detection cassette 24 while a radiation image signal is being read out from radiation detector 40 include, for example, a receive error signal. More specifically, when a radiation image signal is transmitted from radiation detection cassette 24 to console 28, it is transmitted in blocks of a predetermined length. Console 28 receives the blocked radiation image signal and determines whether or not each block of radiation image signal is received correctly by parity check or the like. If a receive error is detected in a certain block of radiation image signal, console 28 outputs a control signal to request retransmission of the errored block of radiation image signal to radiation detection cassette 24. In the description above, the control signal is outputted from console 28 to radiation detection cassette 24 only when a receive error is detected, but either one of signals indicating correct reception and error detection may always be outputted for each block.

Radiation detector 40 included in radiation detection cassette 24 in the radiation image photographing system according to the present embodiment is a detector that directly converts radiation X incident thereon by photoelectrical conversion layer 51, but it is not limited to this and a so-called indirect type radiation detector may also be used in which radiation X incident thereon is convert to visible light by a scintillator and then the visible light is converted to an electrical signal using amorphous silicon (a-Si) or the like as described, for example, in Patent Document 1.

Further, radiation detector 40 is a so-called TFT readout type radiation detector in which a charge signal is read out by TFT, but it is not limited to this and a so-called optical readout type radiation detector may also be used in which a stored charge signal is read out by irradiating readout light as described, for example, in Japanese Unexamined Patent Publication No. 2000-105297.

What is claimed is:

1. A radiation image detection apparatus, comprising a radiation detection unit that generates a charge by receiving radiation transmitted through a subject to detect a radiation image of the subject, a readout unit that reads out a radiation image signal representing the radiation image from the radiation detection unit, and a radio communication unit that outputs a radiation image signal read out from the readout unit as a radio communication signal,
wherein the radio communication unit is a unit that causes the carrier frequency of the radio communication signal to become lower during a reading period in which the radiation image signal is being read out by the readout unit than the carrier frequency of the radio communication signal at a time other than during the reading period.

2. The radiation image detection apparatus as claimed in claim 1, wherein the reading period is a period in which a motion image of the subject is being detected by the radiation detection unit.

3. The radiation image detection apparatus as claimed in claim 2, wherein the radio communication unit is a unit that outputs a signal other than the radiation image signal as a radio communication signal, and causes the carrier frequency of the radio communication signal to become lower for the signal other than the radiation image signal than the carrier frequency of the radio communication signal for the radiation image signal during the reading period.

4. The radiation image detection apparatus as claimed in claim 1, wherein the radio communication unit is a unit that outputs a signal other than the radiation image signal as a radio communication signal, and causes the carrier frequency of the radio communication signal to become lower for the signal other than the radiation image signal than the carrier frequency of the radio communication signal for the radiation image signal during the reading period.

5. A radiation image photographing system, comprising:
a radiation image detection apparatus having a radiation detection unit that generates a charge by receiving radiation transmitted through a subject to detect a radiation image of the subject, a readout unit that reads out a radiation image signal representing the radiation image from the radiation detection unit, and a radio communication unit that outputs a radiation image signal read out from the readout unit as a radio communication signal; and
a photographing control apparatus that outputs at least one of a signal indicating still image photographing, a signal indicating preview image photographing, and a signal indicating motion image photographing to the radiation image detection apparatus, wherein:
the radiation image detection apparatus includes a photographing mode signal receiving unit that receives the signal outputted from the photographing control apparatus; and
the radio communication unit is a unit that causes the carrier frequency of the radio communication signal to become lower, when the signal indicating preview image photographing or the signal indicating motion image photographing is received, than the carrier frequency of the radio communication signal when the signal indicating still image photographing is received.

* * * * *